(12) United States Patent
Khan

(10) Patent No.: US 12,090,121 B1
(45) Date of Patent: Sep. 17, 2024

(54) PNEUMATIC STERILE LIQUID COMPOUNDING MACHINE

(71) Applicant: Akbar Khan, Delray Beach, FL (US)

(72) Inventor: Akbar Khan, Delray Beach, FL (US)

( * ) Notice: Subject to any disclaimer, the term of this patent is extended or adjusted under 35 U.S.C. 154(b) by 0 days.

(21) Appl. No.: 18/637,939

(22) Filed: Apr. 17, 2024

(51) Int. Cl.
*A61J 3/00* (2006.01)

(52) U.S. Cl.
CPC .................................... *A61J 3/002* (2013.01)

(58) Field of Classification Search
CPC ....................................................... A61J 3/002
USPC ............................................................ 141/329
See application file for complete search history.

(56) References Cited

U.S. PATENT DOCUMENTS

| | | |
|---|---|---|
| 6,360,794 B1 | 3/2002 | Turner |
| 8,167,837 B2 | 5/2012 | Judd et al. |
| 10,980,710 B2 * | 4/2021 | Tasaka ................. B01F 35/422 |
| 2009/0038709 A1 * | 2/2009 | VanVreeland ........ B01F 31/201 |
| | | 141/18 |
| 2014/0020790 A1 * | 1/2014 | Yuyama ..................... A61J 1/20 |
| | | 141/27 |
| 2023/0263958 A1 | 8/2023 | Payeli et al. |

FOREIGN PATENT DOCUMENTS

| | | |
|---|---|---|
| KR | 100597814 B1 | 7/2006 |
| KR | 20140054812 A | 5/2014 |

* cited by examiner

*Primary Examiner* — Jason K Niesz
(74) *Attorney, Agent, or Firm* — Kenyon Jenckes

(57) ABSTRACT

In an embodiment, a user operated pneumatic sterile liquid compounding device enables a user to easily and rapidly perform a sterile liquid compounding operation. The frame of the device is configured to receive a syringe with a needle inserted into a sterile vial. A pneumatic cylinder including a pusher rod connected to a pusher plate engages the top of the syringe plunger. Initially a user-operated lever is in an "UP" position. When the lever is moved to a "DOWN" position, the device engages the pusher plate to move the plunger down to inject the liquid in the syringe into the sterile container. The compounding device is powered by pressured gas from a cartridge via an adjustable pressure regulator, a pressure release valve, and a pneumatic cylinder valve connected to the pneumatic cylinder to allow pressured gas applied to the pneumatic cylinder to raise and lower the rod.

10 Claims, 3 Drawing Sheets

PNEUMATIC STERILE LIQUID COMPOUNDING MACHINE

TECHNICAL FIELD

The technical field of the disclosed embodiments relate to sterile liquid compounding, and more particularly to user-operated liquid compounding machines.

BACKGROUND

Liquid compounding is a crucial process in pharmaceutical and research settings, allowing for the preparation of medications and solutions tailored to specific patient needs or experimental requirements. Traditionally, this process involves manually introducing an unsterile liquid into a syringe and filtering it into a sterile vial. While feasible for small-scale operations, manual compounding becomes impractical and potentially hazardous when larger batches are required.

One significant concern with manual liquid compounding is the risk of fatigue and repetitive stress injuries among operators. Performing repetitive tasks over extended periods can lead to physical strain and discomfort, increasing the likelihood of errors and accidents. Moreover, the time and effort required for manual compounding can slow down the production process, impacting efficiency and productivity.

To address these challenges, automated liquid compounding machines have been developed. These computer-operated systems streamline the compounding process, reducing the need for manual intervention and minimizing the risk of operator fatigue and injuries. However, existing automated systems are often large, complex, and expensive, making them impractical for smaller operations such as small pharmacies, infusion clinics or research laboratories with limited resources and space.

SUMMARY

In an embodiment, a pneumatic sterile liquid compounding device includes a frame, preferably constructed from a non-corrosive material with any crevices sealed with a sealant. The frame may include a syringe flange support configured to receive a syringe assembly. The syringe assembly may include a syringe with a barrel and a flange at a top (proximal) end, normally used for a person to grip while pressing down on a plunger to eject a liquid in the barrel. At the bottom of the syringe barrel, a hydrophilic filter may be connected to a syringe needle via a Luer lock. The syringe needle may be inserted into a sterile container. A hydrophobic vent filter including a needle may also be also inserted into the sterile container to vent gases exhausted as the liquid, e.g., an unsterilized medicine, is injected into the sterile container. The vent filter prevents bacteria from being introduced into the sterile container via the venting needle.

The syringe, including the syringe needle and vent filter needle inserted into the vial, may be positioned in the compounding device and held in place by a syringe holder that engages the flange of the syringe and a base of the frame configured to accommodate the sterile container (e.g., vial).

A pneumatic cylinder including a pusher rod may be connected to a pusher plate may engage the top of the syringe plunger. The machine may be actuated by a user-operator. Initially the lever is in an "UP" position corresponding with the pusher plate at its highest position. When moved to a "DOWN" (lowest) position, the device may engage the pusher plate to move the plunger down to inject the liquid in the syringe into the sterile container.

In operation, the compounding device is powered by pressured gas (e.g., CO2) from a cartridge via an adjustable pressure regulator, a pressure release valve, a pneumatic cylinder valve, e.g., a 4 or 5/2 way valve, connected to the pneumatic cylinder to allow pressured gas applied to the pneumatic cylinder to raise and lower the rod, and connected pusher plate between an upper position and a lower position.

An exhaust manifold may be connected to the pneumatic cylinder with a hydrophobic exhaust filter to sterilize exhausted gas.

A gauge may be connected to the pressure regulator to enable the user to observe the pressure and make adjustments as necessary.

The various filters may be, for example, 0.2 micron filters.

DETAILED DESCRIPTION

Figure 1:
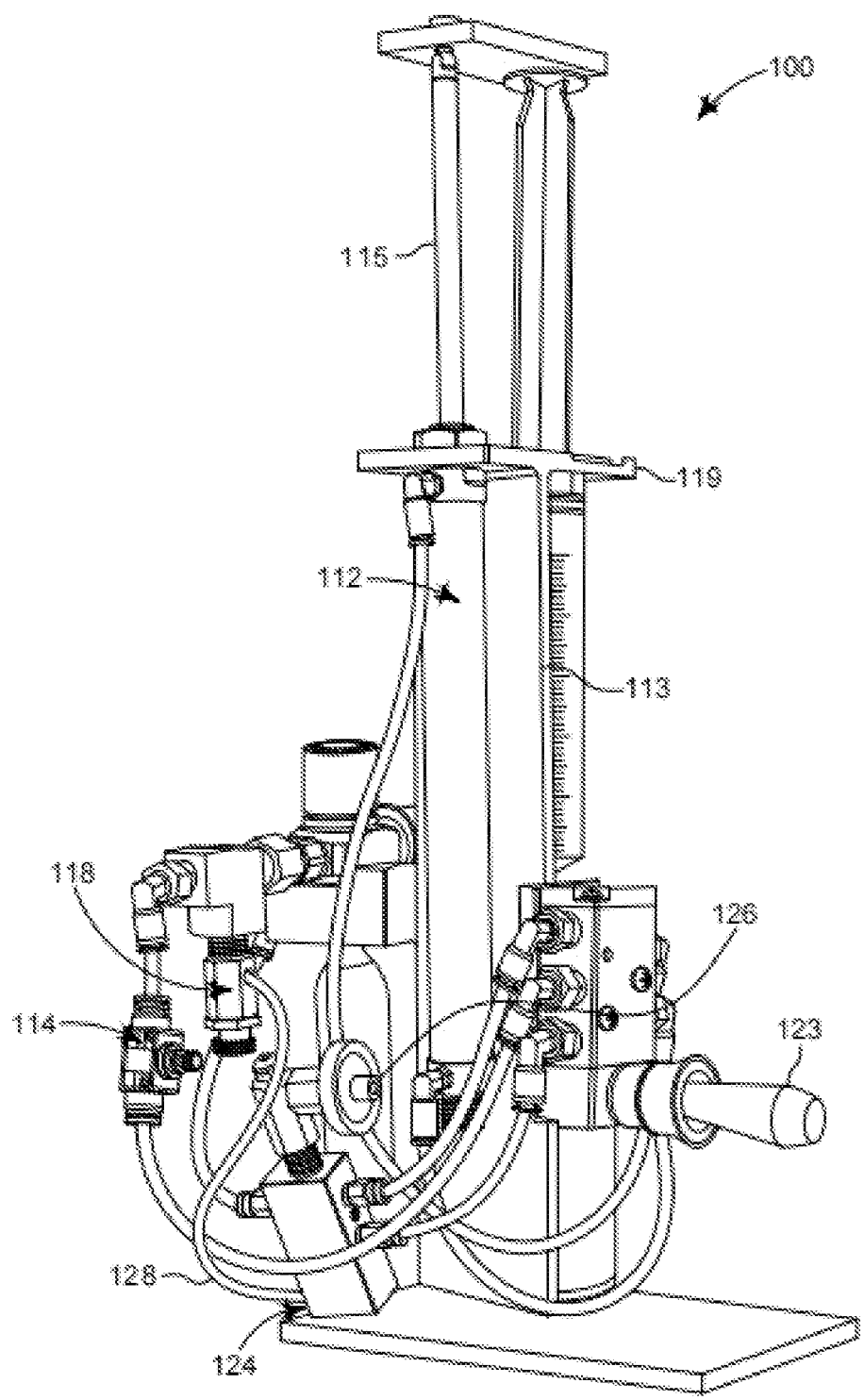
FIG. 1 is a front view of a compounding machine according to an embodiment.
Figure 2:
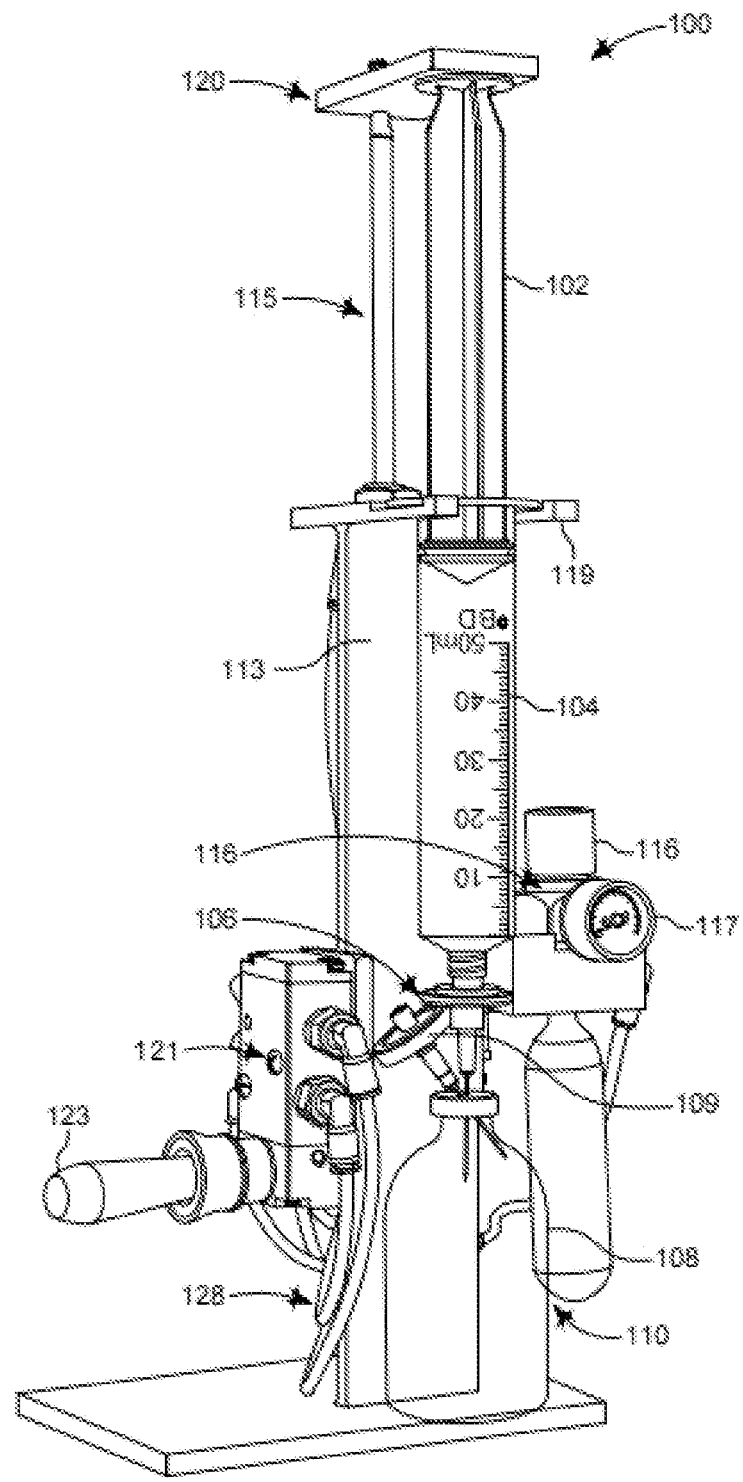
FIG. 2 is a rear view of the compounding machine of FIG. 1 according to an embodiment.
Figure 3:
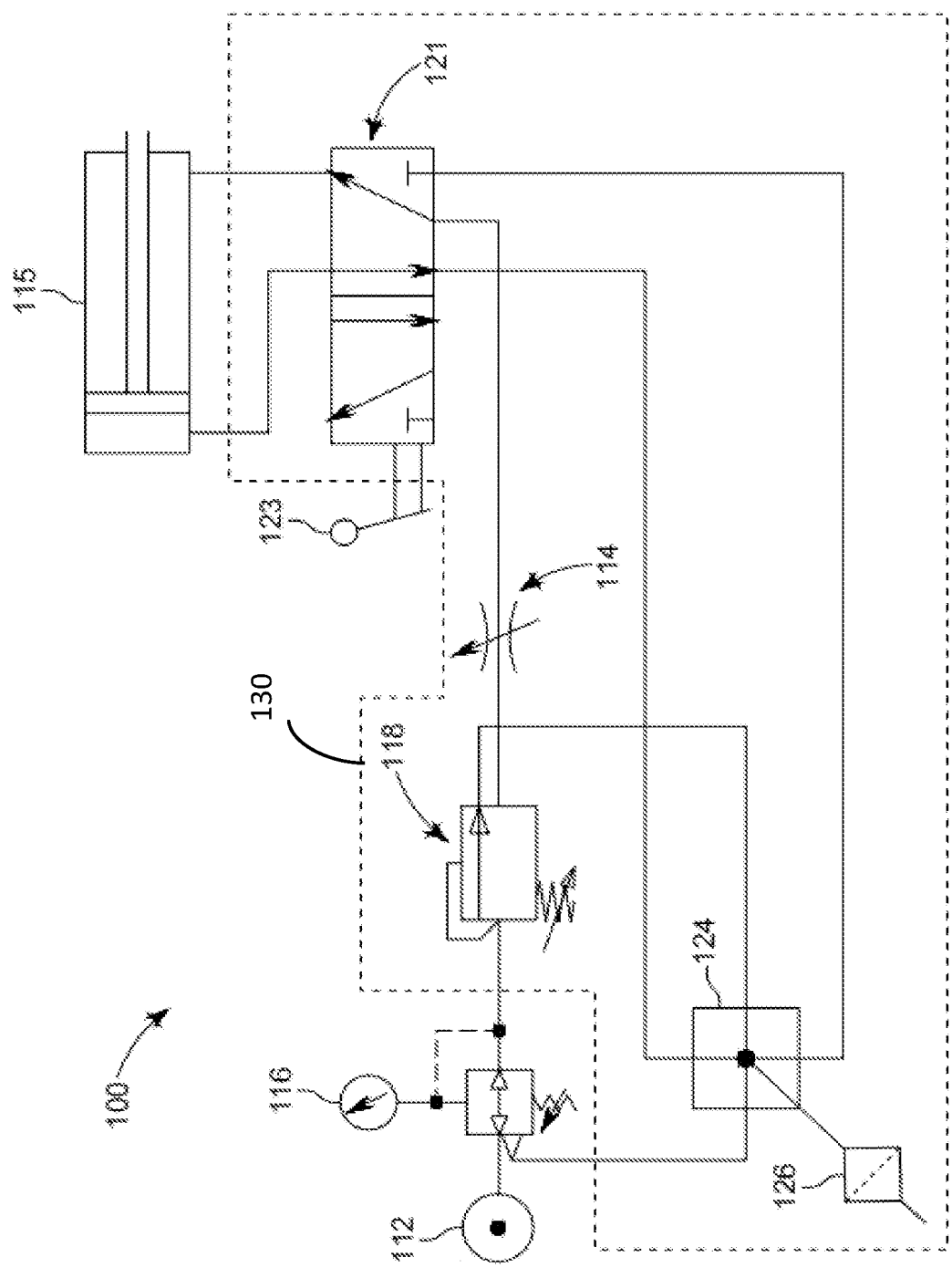
FIG. 3 is a schematic diagram of the compounding machine of FIG. 1 according to an embodiment.

FIGS. 1, 2 and 3 show a front view, rear view, and a schematic diagram, respectively, of a compounding machine 100 designed to enable pharmacists, doctors, or other health practitioners to produce sterile liquid medications which require sterilization with a hydrophilic antimicrobial filter. The compounding machine 100 partially automates the compounding process when low volumes of sterile medications need to be produced. An advantage provided by the compounding machine 100 is the prevention of fatigue or repetitive use injury when pushing a syringe by hand to filter the liquid medication. It can also improve an individual's health and safety and increase productivity by providing a faster, more efficient workflow.

The machine 100 operates by using compressed gas to push the plunger 102 of a syringe 104 filled with an unsterile liquid medication through a hydrophilic antimicrobial filter 106, e.g., a 0.2 micron filter, fit with a suitable bore needle 107, e.g. a #21-#23 gauge needle, and into a sterile container 108, such as a sterile glass vial with a synthetic rubber cap via the bore needle 107. A hydrophobic pressure release filter 109 may include a small needle with a hydrophobic filter, e.g., 0.2 micron filter, to allow air/gas to exit the sterile container 108 when liquid is introduced into the container, and prevent bacteria from being introduced into the sterile container.

Compressed gas (e.g. CO2) in a cartridge 110 powers the machine. A double-action pneumatic cylinder 112 is mounted in a frame, e.g., a non-corroding metal frame 113 constructed from, e.g. aluminum or stainless steel. The flow rate of compressed gas transferred to the pneumatic cylinder may be controlled by an adjustable flow control valve 114 to prevent sudden movements of a pneumatic cylinder rod 115.

The maximum pressure of gas from the gas cartridge is controlled by an adjustable gas pressure regulator 116 (e.g., relieving type, approx 0-80 psi) including a pressure gauge 117. Pressure must be set below the maximum allowable pressure for the hydrophilic antimicrobial filter 106 used to sterilize the liquid medication. A pressure relief valve 118 prevents accidental application of excess pressure to the syringe 104 and hydrophilic antimicrobial filter 106 to prevent damage (e.g. in the event of a failure of the pressure regulator).

The syringe 104 may be secured in the compounding machine by placing the flange of the syringe cylinder over a syringe holder 119. The relieving design of the pressure regulator 116 prevents excess pressure being applied to the filter if the operator manually pushes on a syringe pusher plate 120.

A pneumatic valve 121, e.g., a 4-way or 5-way/2 position type, allows pressurized gas to be applied to the pneumatic cylinder 112 to either raise or lower the syringe pusher plate. An operator-controlled lever 123 connected to the pneumatic valve 121 can be manually moved between an up and down position to mirror the up/down movement of the syringe pusher plate.

All sources of exhausted gas may be routed to an exhaust manifold 124 and passed through a hydrophobic filter 126, e.g., a 0.2 micron filter, to ensure that the exhausted gas is sterile This allows the compounding machine to be used in a sterile environment, for example, in a laminar flow hood of a biological safety cabinet, without compromising sterility. A pneumatic connecting line 128 may be connected between the pressure relief valve 118 and the exhaust manifold 124.

The compounding machine 100 preferably includes smooth, non-corroding surfaces, without crevices where bacteria can adhere. Any crevices may be filled with suitable sealant.

In an embodiment, the compounding machine 100 may first be sterilized by cleaning with a disinfectant solution, e.g. 70% isopropyl alcohol, and placed in a laminar flow hood prior to initiating a sterilized liquid compounding operation.

To prepare for a compounding operation, the operator may fill the syringe 104 (e.g. 60 ml) with an unsterile medication to be sterilized by filtration. Next, the hydrophilic antimicrobial filter 106 and the bore needle 107 may be attached to the syringe via, e.g., a Luer lock connector, forming a syringe/filter/needle assembly.

The operator inserts the bore needle 107 into the sterile container 108 and then mounts an assembly including the filled syringe, filter, and sterile container in the compounding machine 100 with the syringe pusher plate 120 in an upper ("UP") position, i.e., with the pusher plate 120 in its highest position, as shown in FIG. 2. The operator may also insert the needle of the hydrophobic pressure release filter 109 into the container to vent air from the vial during operation.

The operator may set, or confirm that, the pressure in the compounding machine 100 is less than the maximum recommended pressure for the hydrophilic filter 106 via the pressure regulator 116 and gauge 117.

By manually operating lever 123, the operator may then set the pneumatic valve 122 to a lower position ("DOWN") position to control the pneumatic cylinder 112 and rod 115 connected to the pusher plate 120 to lower the syringe pusher plate and push the liquid, e.g., medication, through the filter into the sterile vessel. When the contents of the syringe have passed through the filter, the operator may manually set the pneumatic valve 121 to the UP position via the lever 123 to raise the syringe pusher plate for a subsequent operation.

The syringe/filter/needle assembly and the filled container 108 may then be removed from the machine and the operation repeated as needed.

When the compressed gas cartridge 110 is empty, it can be replaced with a new cartridge.

In an alternative embodiment, the compounding device may include a plastic or non-corroding metal cover 123 designed to encapsulate the tubing, relief valve, manifold, and cylinder, as shown in FIG. 3. This cover serves the purpose of facilitating sterilization procedures prior to insertion into a laminar flow hood, thereby ensuring compliance with sterilization standards. By enclosing critical components within a sterilizable casing, cleaning and sterilizing the machine 100 becomes easier to enhance operational hygiene and minimize the risk of contamination during pharmaceutical compounding processes.

| Reference numbers: | |
|---|---|
| 100 | Compounding machine |
| 102 | Plunger |
| 104 | Syringe |
| 106 | Hydrophilic antimicrobial filter |
| 107 | Bore needle |
| 108 | Sterile container |
| 109 | Hydrophobic pressure release filter |
| 110 | Gas cartridge |
| 112 | Pneumatic cylinder |
| 113 | Frame |
| 114 | Flow control valve |
| 115 | Rod |
| 116 | Gas pressure regulator |
| 117 | Pressure gauge |
| 118 | Pressure relief valve |
| 119 | Syring holder |
| 120 | Syringe pusher plate |
| 121 | Pneumatic valve |
| 122 | Pneumatic valve control switch |
| 123 | Lever |
| 124 | Exhaust manifold |
| 126 | Hydrophobic exhaust filter |
| 128 | Pneumatic connecting line |
| 130 | Cover |

The foregoing method descriptions and figures are provided as illustrative examples only. The order of operations in the aspects described herein may be performed in one or more other orders. Words such as "thereafter," "then," "next," etc. are used to guide the reader through the description of the methods and systems described herein, and do not limit the order of the operations. Any reference to claim elements in the singular, for example, using the articles "a," "an," or "the" is not to be construed as limiting the element to the singular. Also, relative terms such as "top," "bottom," "upper," "lower," "up," "down", "above," "below," and the like as used herein describe the relative positions of elements or features, and are not limited to the orientations depicted in the drawings. As used herein, the terms "user" and "operator" are interchangeable. Furthermore, the specific dimensions and other details set forth with regard to specific embodiments are for illustrative purposes only and are not intended to limit the scope of the claims.

The preceding description of the disclosed aspects is provided to enable any person skilled in the art to make, implement, or use the claims. Various modifications to these aspects will be readily apparent to those skilled in the art, and the generic principles defined herein may be applied to other aspects without departing from the scope of the claims. Thus, the present disclosure is not intended to be limited to the specific embodiments described herein but is to be accorded the widest scope consistent with the claims.

The invention claimed is:

1. A pneumatic sterile liquid compounding device comprising:
   a frame including,
      a syringe flange support configured to receive a syringe assembly including a syringe including a barrel with a flange at a distal end and a proximal end, a hydrophilic filter connected to the end of the barrel and connected to a syringe needle, and a sterile container, wherein the syringe needle is inserted into a sterile container, and
      a base configured to support the sterile container;
   a pneumatic cylinder;
   a rod connected to the pneumatic cylinder;
   a pusher plate connected to the rod;
   an adjustable pressure regulator;
   a pressure release valve connected to the adjustable pressure release regulator;
   a cartridge connector connected between the pneumatic cylinder and the adjustable pressure regulator, the cartridge connector configured to allow a cartridge containing a pressurized gas to be removably connected;
   a pneumatic cylinder valve connected to the pneumatic cylinder, said valve operative to allow pressured gas applied to the pneumatic cylinder to raise and lower the rod,
   wherein the pneumatic cylinder valve is operative to control the pneumatic cylinder to move the rod and connected pusher plate between an upper position and a lower position;
   a manually operated lever connected to the pneumatic cylinder valve and configured to enable an operator to control the rod between the upper position and the lower position;
   an exhaust manifold connected to the pneumatic cylinder; and
   a hydrophobic exhaust filter connected to the exhaust manifold and operative to sterilize exhausted gas.

2. The pneumatic sterile liquid compounding device of claim 1, wherein the hydrophobic exhaust filter comprises a 0.2 micron filter.

3. The pneumatic sterile liquid compounding device of claim 1, further comprising a gauge connected to the pressure regulator.

4. The pneumatic sterile liquid compounding device of claim 1, wherein the frame comprises a non-corrosive material.

5. The pneumatic sterile liquid compounding device of claim 1, wherein the frame includes crevices sealed with a sealant.

6. The pneumatic sterile liquid compounding device of claim 1, wherein the pneumatic valve is a 2-position type valve.

7. The pneumatic sterile liquid compounding device of claim 1, further comprising the syringe assembly.

8. The pneumatic sterile liquid compounding device of claim 7, wherein the hydrophilic filter comprises a 0.2 micron filter.

9. The pneumatic sterile liquid compounding device of claim 7, further comprising a hydrophobic vent filter including a needle inserted into the sterile container.

10. The pneumatic sterile liquid compounding device of claim 9, wherein the hydrophobic vent filter comprises a 0.2 micron filter.

* * * * *